US011666216B2

(12) United States Patent
Scherer et al.

(10) Patent No.: US 11,666,216 B2
(45) Date of Patent: Jun. 6, 2023

(54) WIRELESS AUTOMATED ANIMAL MONITORING SYSTEM

(71) Applicant: CALIFORNIA INSTITUTE OF TECHNOLOGY, Pasadena, CA (US)

(72) Inventors: Axel Scherer, Barnard, VT (US); Peter A Petillo, Lawrence, KS (US); Samson Chen, Pasadena, CA (US); Azita Emami, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 452 days.

(21) Appl. No.: 15/987,843

(22) Filed: May 23, 2018

(65) Prior Publication Data

US 2018/0338681 A1   Nov. 29, 2018

Related U.S. Application Data

(60) Provisional application No. 62/548,050, filed on Aug. 21, 2017, provisional application No. 62/510,574, filed on May 24, 2017.

(51) Int. Cl.
*A61B 5/00* (2006.01)
*A01K 1/03* (2006.01)
(Continued)

(52) U.S. Cl.
CPC .............. *A61B 5/002* (2013.01); *A01K 1/031* (2013.01); *A01K 11/006* (2013.01); *A01K 29/00* (2013.01);
(Continued)

(58) Field of Classification Search
CPC ......... A61B 5/002; A61B 5/1113; A61B 5/01; A61B 5/14532; A61B 5/14539;
(Continued)

(56) References Cited

U.S. PATENT DOCUMENTS 9,867,539 B2 * 1/2018 Heikenfeld ............. G06F 19/00
2004/0180391 A1 * 9/2004 Gratzl ................ A61B 5/14532
435/14

(Continued)

FOREIGN PATENT DOCUMENTS

WO   2009/097357 A1   8/2009
WO   2010/144494 A2   12/2010
(Continued)

OTHER PUBLICATIONS

Chaimanonart et al. (Adaptive RF power control for wireless implantable bio-sensing network to monitor untethered laboratory animal real-time biological signals, IEEE Sensors, 2008 conference) (Year: 2008).*

(Continued)

*Primary Examiner* — Jacqueline Cheng
*Assistant Examiner* — Tho Q Tran
(74) *Attorney, Agent, or Firm* — Steinfl + Bruno, LLP

(57) ABSTRACT

A smart cage includes radiofrequency transceivers and tags attached to laboratory animals. The tags include sensors to detect monitorable conditions of the laboratory animals. The sensors include working electrodes, counter electrodes, reference electrodes, and potentiostats. The top surface of the electrodes is coated with ionophores or enzymes which detect the monitorable conditions of the laboratory animals.

22 Claims, 8 Drawing Sheets

(51) Int. Cl.
| | |
|---|---|
| *A01K 11/00* | (2006.01) |
| *A01K 29/00* | (2006.01) |
| *A61B 5/11* | (2006.01) |
| *H04B 5/00* | (2006.01) |
| *A61B 5/145* | (2006.01) |
| *A61B 5/1486* | (2006.01) |
| *A61B 5/01* | (2006.01) |

(52) U.S. Cl.
CPC .......... *A61B 5/1113* (2013.01); *H04B 5/0075* (2013.01); *A61B 5/01* (2013.01); *A61B 5/1486* (2013.01); *A61B 5/14532* (2013.01); *A61B 5/14539* (2013.01); *A61B 5/14542* (2013.01); *A61B 5/14546* (2013.01); *A61B 5/14865* (2013.01); *A61B 5/6832* (2013.01); *A61B 5/6868* (2013.01); *A61B 2503/40* (2013.01); *A61B 2503/42* (2013.01)

(58) Field of Classification Search
CPC ............ A61B 5/14542; A61B 5/14546; A61B 5/1486; A61B 5/14865; A61B 5/6832; A61B 5/6868; A61B 2503/40; A61B 2503/42; A01K 1/031; A01K 11/006; A01K 29/00; H04B 5/0075
USPC ........................................................ 600/345
See application file for complete search history.

(56) References Cited

U.S. PATENT DOCUMENTS

| | | | |
|---|---|---|---|
| 2006/0110049 A1 | 5/2006 | Liang et al. | |
| 2007/0016381 A1* | 1/2007 | Kamath | A61B 5/1495 702/19 |
| 2007/0077265 A1* | 4/2007 | Klueh | C12N 5/0062 424/423 |
| 2007/0244374 A1 | 10/2007 | Vyssotski et al. | |
| 2007/0296393 A1* | 12/2007 | Malpas | H02J 50/402 323/355 |
| 2009/0243584 A1* | 10/2009 | Zhang | B81C 1/00031 324/71.1 |
| 2010/0055728 A1 | 3/2010 | Yang et al. | |
| 2010/0222686 A1 | 9/2010 | Fisher et al. | |
| 2011/0130804 A1* | 6/2011 | Lin | A61N 1/36146 607/45 |
| 2012/0212149 A1* | 8/2012 | Forster | H05B 47/19 315/246 |
| 2012/0302858 A1* | 11/2012 | Kidmose | A61B 5/0476 600/379 |
| 2014/0018639 A1 | 1/2014 | Jamieson et al. | |
| 2014/0247004 A1* | 9/2014 | Kari | H02J 7/025 320/106 |
| 2016/0213317 A1* | 7/2016 | Richardson | A61B 5/1135 |
| 2018/0160649 A1* | 6/2018 | Hicks | A01K 39/012 |

FOREIGN PATENT DOCUMENTS

| | | |
|---|---|---|
| WO | 2010/144494 A3 | 12/2011 |
| WO | 2017/054933 A1 | 4/2017 |

OTHER PUBLICATIONS

A. Agarwal et al., Wireless Power Transfer Strategies for Implantable Bioelectronics, IEEE Reviews in Biomedical Engineering, vol. 10, pp. 136-161 (Year: 2017).*
B. Taalla et al., A Review on Miniaturized Ultrasonic Wireless Power Transfer to Implantable Medical Devices, IEEE Access, vol. 7, pp. 2092-2106. (Year: 2019).*
C. Soltani et al., Low-Radiation Cellular Inductive Powering of Rodent Wireless Brain Interfaces: Methodology and Design Guide, IEEE Transactions on Biomedical Circuits and Systems, vol. 10, No. 4, pp. 920-932, Aug. 2016.*
D. Kilinc et al., A System for Wireless Power Transfer of Micro-Systems In-Vivo Implantable in Freely Moving Animals, IEEE Sensors Journal, vol. 14, No. 2, pp. 522-531, Feb. 2014.*
E. Lee et al., A Smart Wirelessly Powered Homecage for Long-Term High-Throughput Behavioral Experiments, IEEE Sensors Journal, vol. 15, No. 9, pp. 4905-4916, Sep. 2015.*
Besnoff et al., Near field modulated backscatter for in vivo biotelemetry, 2012 IEEE International Conference on RFID (RFID) (Year: 2012).*
Bayne KA. 2005. Potential for unintended consequences of environmental enrichment for laboratory animals and research results. ILAR Journal, vol. 46, No. 2: pp. 129-139.
Bickler, P.; Feiner, J.; Rollins, M.; Meng, L., Tissue Oximetry and Clinical Outcomes, Anesthesia and Analgesia, Jan. 2017, 124 (1), pp. 72-82.
"Directive 2010/84/EU, Article 101" Ec.Europa.Eu., Official Journal of the European Union, Dec. 2010, pp. L 348/74 to L 348/99, 27 pgs.
Benaroya-Milshtein N, Hollander N, Apter A, Kukulansky T, Raz N, Wilf A, Yaniv I, Pick CG. Environmental enrichment in mice decreases anxiety, attenuates stress responses and enhances natural killer cell activity. Jun. 2004. Eur J Neurosci 20: pp. 1341-1347.
Belz EE, Kennell JS, Czambel RK, Rubin RT, Rhodes ME. Environmental enrichment lowers stress-responsive hormones in singly housed male and female rats. Pharmacology, Biochemistry and Behavior. Sep. 2003. 76: pp. 481-486.
International Search Report issued for International Patent Application No. PCT/US2018/034228, filed on May 23, 2018 on behalf of California Institute of Technology, dated Sep. 10, 2018. 6 pages.
Kalliokoski O, Jacobsen KR, Darusman HS, et al. Mice Do Not Habituate to Metabolism Cage Housing—A Three Week Study of Male BALB/c Mice. Reddy H, ed. PLoS ONE. Mar. 2013;8(3):e58460. doi:10.1371/journal.pone.0058460. pp. 1-11.
Lubbers, D. W., Oxygen electrodes and optodes and their application in vivo. Advances in experimental medicine and biology, 1996, 388, pp. 13-34.
National Research Council. 2011.Guide for the Care and Use of Laboratory Animals: Eighth Edition. Washington, DC: The National Academies Press. https://doi.org/10.17226/12910. 247 pgs.
Novak MA, Meyer JS, Lutz C, Tiefenbacher S. 2006. Deprived environments: Developmental insights from primatology. In: Mason G, Rushen J, eds. Stereotypic Animal Behaviour: Fundamentals and Applications to Welfare. Wallingford, UK: CABI. p. 153-189.
OET Bulletin 65 (Edition 97-01), Supplement C (Edition 01-01) [Federal Communications Commission Office of Engineering & Technology; Evaluating Compliance with FCC Guidelines for Human Exposure to Radiofrequency Electromagnetic Fields, OET Bulletin 65, Edition 97-01, Aug. 1997] 84 pgs.
Sakr, Y., Techniques to assess tissue oxygenation in the clinical setting. Transfusion and Apheresis Science, 2010, 43 (1), pp. 79-94.
Written Opinion issued for International Patent Application No. PCT/US2018/034228, filed on May 23, 2018 on behalf of California Institute of Technology, dated Sep. 10, 2018. 11 pages.
Extended [Supplementary] European Search Report for EP Application No. 18806443.0 filed on Nov. 11, 2019, on behalf of California Institute of Technology, dated Jan. 21, 2021. 10 Pages.
Volk, Tobias; et al., "RFID Technology for Continuous Monitoring of physiological Signals in Small Animals", IEEE Transactions on Biomedical Engineering, IEEE Service Center, Piscataway, NJ, USA, vol. 62, No. 2, pp. 618-626; ISSN 0018-9294. Feb. 2015. 9 Pages.

* cited by examiner

WIRELESS AUTOMATED ANIMAL MONITORING SYSTEM

CROSS REFERENCE TO RELATED APPLICATIONS

The present application claims priority to U.S. Provisional Patent Application No. 62/510,574, filed on May 24, 2017, and U.S. Provisional Patent Application No. 62/548,050, filed on Aug. 21, 2017, the disclosures of both being incorporated herein by reference in their entirety.

STATEMENT OF INTEREST

This invention was made with government support under Grant No. HR0011-15-2-0050 awarded by DARPA. The government has certain rights in the invention.

TECHNICAL FIELD

The present disclosure relates to monitoring of laboratory animals. More particularly, it relates to a wireless automated animal monitoring system.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
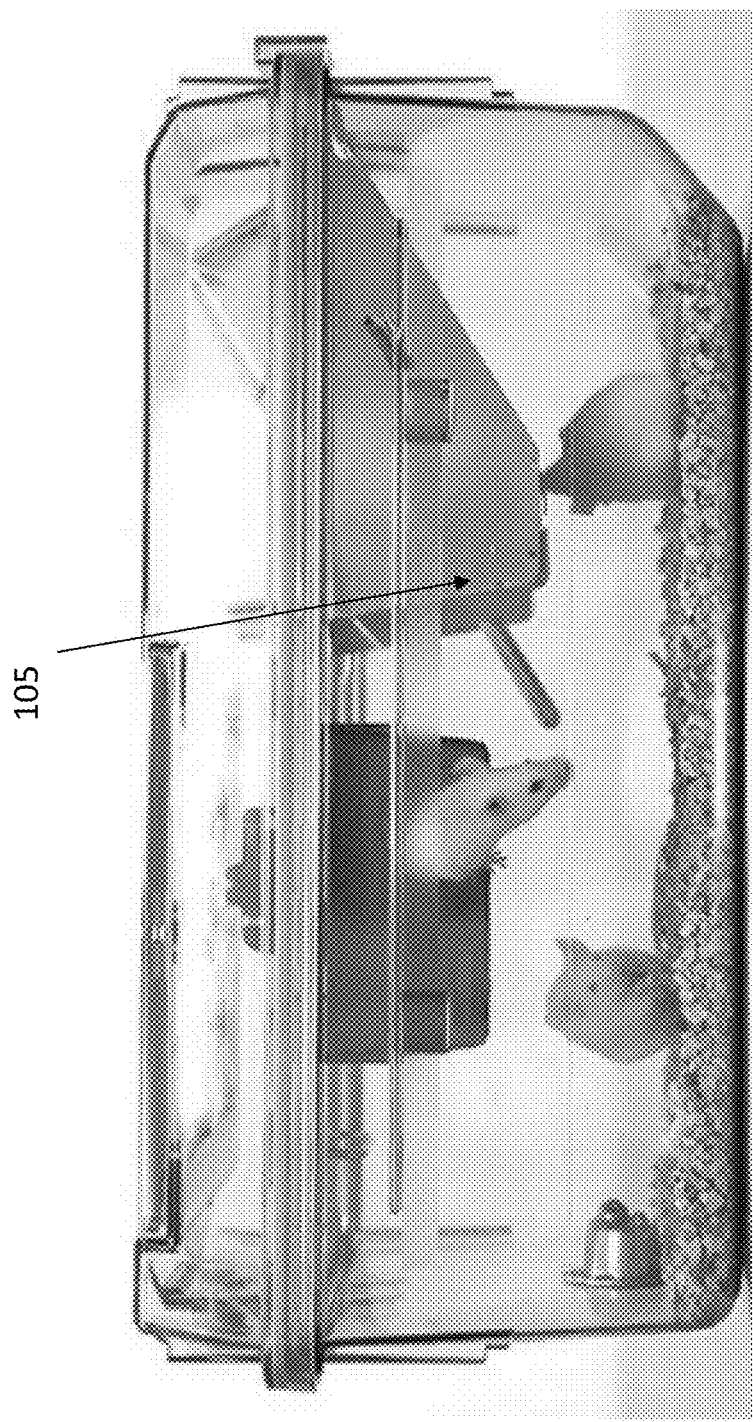
FIG. 1 illustrates a prior art cage for laboratory animals.

In a first aspect of the disclosure, a system is described, the system comprising: a container configured to contain at least one laboratory animal, the container comprising at least one radiofrequency transceiver; and at least one sensor configured to read at least one monitorable condition of the at least one laboratory animal, the at least one sensor configured to be attached to the at least one laboratory animal, the at least one sensor comprising at least one radiofrequency transmitter.

In a second aspect of the disclosure, a method is described, the method comprising: providing a container configured to contain at least one laboratory animal, the container comprising at least one radiofrequency transceiver; providing at least one sensor configured to read at least one monitorable condition of the at least one laboratory animal, the at least one sensor configured to be attached to the at least one laboratory animal, the at least one sensor comprising at least one radiofrequency transmitter; attaching or implanting the at least one sensor to the at least one laboratory animal; and detecting at least one monitorable condition in the at least one laboratory animal by the at least one radiofrequency transceiver communicating with the at least one radiofrequency transmitter.

In a third aspect of the disclosure, a system is described, the system comprising: at least one radiofrequency transceiver configured to be attached to a container, the container configured to contain at least one laboratory animal; and at least one sensor configured to read at least one monitorable condition of the at least one laboratory animal, the at least one sensor configured to be attached to the at least one laboratory animal, the at least one sensor comprising at least one radiofrequency transmitter.

DETAILED DESCRIPTION

The present disclosure describes a cage for laboratory animals that enables monitoring of the state of the animals with a wireless electronic system. This type of cage is referred to as a "smart cage" in the present disclosure. The smart cage enables the continuous or semi-continuous monitoring of laboratory animals for pharmacovigilance through wireless interrogation of the metabolic chemistry of the animals. The capabilities of the smart cage are enabled by the recent development of microscale radiofrequency (RF) tag sensors for measuring metabolites, position and temperature in animals.

In other words, animals can be monitored by detecting their position within the cage, or even the body posture, such as prone, or moving, or laying in an unnatural pose. The metabolites of the animals can also be monitored. For example, the glucose level in the blood of the animal could be detected. In some embodiments, the smell of urine and feces could be detected. The temperature of each animal could also be monitored. The smart cage may monitor any single parameter or combination of parameters, depending on the specific application. The parameters may be combined to determine the condition of each animal more accurately. One or more RF tags could be attached to each animal in order to individually monitor each animal in a cage. It can be common, in fact, to group house laboratory animals in cages, as for example rats are gregarious animals that generally fare better in a social group.

In some embodiments, the system monitors metabolic states, or other conditions such as the pose of the animal. These metabolic and non-metabolic states of an animal can be termed "monitorable conditions". These monitorable conditions may be individually and independently selected from the group consisting of, for example, position, gait, posture, temperature, oxygenation, local pH, and the concentration of glucose, lactate, glutamate, histamine, cortisol, NADH, NAD+, cholesterol, xanthine, sarcosine, spermine, glycolate, choline, urate, GABA, lysine, asparate, nicotine, alcohol, ethanol, D-amino acids, 6-hydroxynicotine, oxalate, putrescine, galactose, pyruvate, poly-amines, acyl coenzyme A, glutathione, glycerolphosphate, gamma-glutamyl-putrescine, nucleosides, adenosine, and glycine.

The smart cage systems can be used, for example, for useful automated measurements of endogenous eobiotics including, but not limited to, glucose, lactate, urea, cortisol, histamine, NADH, sodium, potassium and oxygen levels, position, and temperature, in each laboratory animal. As known to the person of ordinary skill in the art, oxygen levels in blood can be detected as described in Refs. [1-3]. The smart cage systems may also be useful in the automated measurements of xenobiotics including, but not limited to, new pharmaceuticals and their metabolites, alcohol, nicotine, THC, cocaine, and opioids. These fully automated measurement and monitoring systems can fundamentally change the nature of laboratory animal testing for adverse drug reactions. The smart cages can provide significantly more data, from each animal, compared to manual monitoring, as the manual monitoring is not carried out constantly or consistently, while the automated system of a smart cage can continuously monitor the animals. In some cases, manual monitoring can also stress the laboratory animals due to handling and testing, such as drawing blood. Therefore, the smart cage can also reduce the stress of the animals during testing as the RF tags can monitor the animals without manual handling except for the initial attachment of the RF sensor. The RF tags can be attached externally, for example with adhesive, and/or glue, and/or with an adhesive band, or they can also be implanted, for example just under the skin of the animal.

The smart cages can therefore improve the quality and quantity of data collected during drug testing with laboratory animals, thus requiring fewer animals to complete a test, as well as shorter trial times. The animals can remain in their normal social setting without disruption of their wake/sleep cycles, a notable improvement. The stress on the animals during monitoring is reduced with the present invention.

As known to the person of ordinary skill in the art, obesity and metabolic dysfunction are risk factors for a number of chronic diseases, such as type 2 diabetes, hypertension, heart disease, stroke, and certain forms of cancers. Animal studies, human population-based epidemiological studies, and clinical studies have suggested that social isolation can induce chronic stress in mammals, and that the period of stress induction can be short. By contrast, a good social support system is known to exert positive effects on the mental and physical well-being of humans and laboratory animals. See, for example, Refs. [4-5]. Chronic social isolation is also known to negatively affect metabolic parameters and food intake in the social isolated animals further increasing the stress on those animals.

Ref [6] provides the following statements regarding rodent species and their social housing needs: "Appropriate social interactions among members of the same species (conspecifics) are essential to normal development and well-being (Bayne et al. 1995; Hall 1998; Novak et al. 2006)."; "Single housing of social species should be the exception and justified based on experimental requirements or veterinary-related concerns about animal well-being. In these cases, it should be limited to the minimum period necessary . . . "; and "The need for single housing should be reviewed on a regular basis by the IACUC and veterinarian".

Social isolation also includes singly housed animals in adjacent cages. For example, individually housed mice had increased adipose mass compared to group-housed mice, despite comparable body weight. The mechanism for the expansion of white adipose tissue mass was site-specific.

Experiments with sensors often require social isolation because of the nature of the measurement modality and the surgeries needed for sensor implantation. The requirement of social isolation can, by its very nature, induce stress on the experimental animal, which in turn may both have negative effects on animal health and induce an experimental confound into the measurement. Long-term deprivation of social contacts may represent a major concern when performing biosensor measurements on rodents.

The present disclosure, when coupled with the sensors described herein, enables the measurement of multiple modalities within a social environment. Monitorable conditions may be individually and independently monitored in either a single rodent within a group-housed, social environment, or simultaneously in multiple animals within a social, group-housed environment. Moreover, since rodents do not habituate to social isolation, even long-term studies on socially isolated animals would be subject to stress and alerted physiologic states which could complicate experimental findings. Studies performed with the present invention are expected to be less susceptible to animal stress and altered experimental data.

The need for monitoring states and conditions of experimental animals is particularly important for the development of new drugs, potential drug candidates and pharmaceuticals. Pharmacovigilance heavily focuses on determining and measuring adverse drug reactions (ADRs). Adverse drug reactions are defined as any response to a drug which is noxious and unintended, including lack of efficacy. The continuous collection of data related to monitorable conditions can aid in the early identification of drug candidates. Such data may also be used to identify the early elimination of drug candidates that will fail further in the drug development cycle. Currently, most data collection of monitorable conditions is not routine, as the development of smart cages and sensors, such as those described in the present disclosure, have yet to be readily available to researchers.

The wireless technology of smart cages can be designed into monitoring cages which can be optimized and tested in collaboration with animal laboratory facilities. In some embodiments, instead of or in addition to glucose and lactate monitoring microsensors, further capabilities can be added, such as measuring urea, various ions, oxygen, and temperature. In other embodiments, microsensors for xenobiotics such as alcohol can be analyzed. In other embodiments, measurement of temperature and various analytes are independently analyzed.

Animal testing for adverse drug reactions of new pharmaceutical products is an important part of the identification and approval process of safe medications. FIG. 1 illustrates a typical cage used to monitor rats. The cage includes a feeder (105) to provide food and water to the test animals. The pharmacovigilance process usually involves preliminary trials on small animals, such as mice and rats, whose health is monitored during the administration of new drugs to identify adverse, unintended, or noxious responses. During these tests, it is necessary to quantitatively monitor and record any changes in the health state of the animals, which generally involves frequent blood draws and measurements of changes in behavior of the animals. Ideally, the animals are kept in their normal social environment and not isolated during the testing procedures, which can require several months. Unfortunately, samples can only be taken intermittently in small animals, as blood draws require significant fluid volumes, and legal limits set the maximum frequency of invasive sample extraction. These limitations in turn lead to the requirement for large cohorts of animals and data that must be statistically correlated. Animal testing is also very labor-intensive, as animals must be removed from their cages, handled, and often anesthetized before sample extraction. The blood draw process is also known to cause stress to animals. Handling of the animals is also known to disrupt their normal circadian cycles, which can lead to unintended bias in the data collected.

With the latest wireless sensor and measurement technology, it is now possible to automate the monitoring of animals during long-term testing and to significantly increase the amount of data gathered. Wireless RF tags are commonly used to identify companion and production animals. For example, RF tags are often implanted under the skin of companion animals, such as dogs and cats. However, these RF tags tend to be too large to be inserted into small laboratory animals such as rats or mice.

For the purpose of monitoring small animals, a smart cage can instead be fabricated with radio-frequency (RF) readers that are optimized to interrogate millimeter-sized RF tags. The RF tags are implanted into the laboratory animals and provide metabolic or non-metabolic readings, while the reader devices are integrated in the smart cage. In other words, the RF tags comprise an electromagnetic wave transmitter, while the smart cage comprises a receiver. Small RF tags and wireless readers as described in the present disclosure include many advantages. For example, it is advantageous to frequently sample the animals without disturbing or distressing the animals by handling and by sample extraction. Individually-tagged devices can be identified and read to differentiate between animals within their normal social setting. In other words, each transmitter can be identified by the receivers, for example through the inclusion in the transmitted message of a code identifying the transmitter, attached to the transmitted data. The stress of animals and staffing are reduced for animal testing when performing 24/7 experiments.

To match the needs of laboratory animal monitoring, sensors must be small and inexpensive. This invention is not limited to any specific wireless sensor design or geometry, although some geometries may have specific advantages over others. The sensors also have to exhibit measurement lifetimes of several months. Until now, it has been difficult to match these requirements. By combining the latest RF tag technology with modern enzyme designs, the present disclosure describes wireless systems that enable the automation of monitoring cages, rendering it possible to observe the health progression of individual animals for the time required to perform drug discovery activities. Said activities can occur over weeks to months.

In some embodiments, RF tag microsensors can measure blood levels of glucose, lactate, urea, sodium, potassium and oxygen, and body temperature. For example, to fabricate an RF microsensor, electrochemically active enzymes or ionophores are coated onto a compact and low-power potentiostat. These sensors perform well over several weeks of measurement, and are small enough that multiple chips can be implanted to simultaneously monitor different parameters in the same animal.

Figure 5:
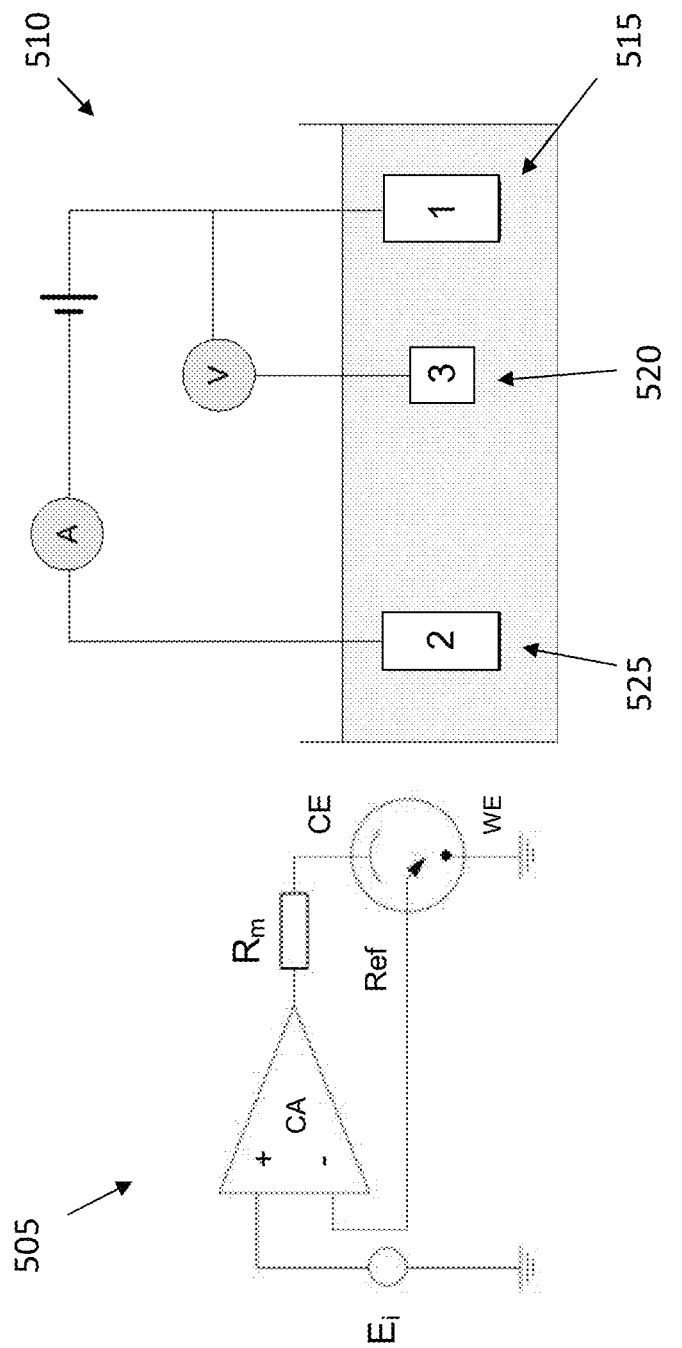
FIG. 5 illustrates exemplary electrical elements.

As known to the person of ordinary skill in the art, a potentiostat is the electronic hardware required to control a three electrode cell and run many electroanalytical experiments. In some embodiments, the microsensor comprises three electrodes and a potentiostat. The potentiostat maintains the potential of the working electrode at a constant level with respect to the reference electrode, by adjusting the current at an auxiliary electrode. The electric circuit diagram of the potentiostat is usually described in terms of simple op amps. For example, an exemplary diagram description of a potentiostat is illustrated in FIG. 5 (505). The three electrode configuration, comprising a working electrode, a reference electrode and an auxiliary electrode, will be known to the person of ordinary skill in the art. For example, FIG. 5 illustrates a possible sensing electrode setup (510), comprising a working electrode (515), a reference electrode (520) and a counter electrode (525).

In some embodiments, a smart cage is outfitted with readers that frequently power and interrogate the microsensors. For example, the reader can transmit power wirelessly to the sensor, through known techniques such as energy transfer through coils. One example of an interrogation protocol by the smart cage is to measure the animal every time that it desires to eat or drink, which for a mouse is approximately every 8-10 minutes while awake. Data obtained through such tests is much more frequent than what is possible under present manual protocols. Such methodology requires precise positioning of the reader with respect to the implanted RF tags, as well as rapid acquisition of data within less than a minute. Such requirements can be met with three-electrode platinum electrochemical potentiostats coated with enzyme coatings. These sensors can measure meaningful and accurate data within seconds, and the wireless RF tags can transmit that data to a reader within even shorter times. Thus, the sampling time is only limited by the rate of metabolic changes within the tested animal.

In some embodiments, the compact wireless microchips have lateral dimensions of approximately a millimeter, though the sensors may be smaller or larger than a millimeter. In some embodiments, the sensors measure glucose or lactate in vivo, require no batteries, communicate with external controllers through electromagnetic data-links, and are powered by on-chip inductive currents. The miniaturized sensors can allow continuous glucose monitoring (CGM) by using post-processing complementary metal-oxide semiconductors (CMOS) electronic circuits. For example, the CMOS circuit can comprise more than 10,000 transistors. The RF tags can be manufactured at a cost of approximately $0.10/sensor, in some embodiments. The electrochemical sensor platforms of the present disclosures have been tested in vivo for CGM and other ion-generating enzyme reactions. In some embodiments, the CGM sensors can cover the 40-450 mg/dl dynamic range required for clinical monitoring of diabetes patients by coating the working electrode with Pt and glucose oxidase in a glutaraldehyde/bovine serum albumin (BSA) layer. In some embodiments, these chips can also measure lactate by using lactate oxidase as the enzyme. The enzyme layer typically generates 5-200 nA of hydrogen peroxide ion current that is used to determine the concentration of glucose or lactate, though the current may be smaller or larger.

In some embodiments, the approximately millimeter-sized inductively coupled implants, with 10,000 transistors on board, can report the measured current through up to 5 mm thick tissue to a reader located next to the skin, for example in the smart cage. The functions of the reader include: (a) supplying power to the implanted chip through near-field inductive coupling, (b) collecting data by using an active RF-tag approach, and (c) transmitting that information to a computer or smart phone for display, for example through a Bluetooth™ wireless interface. Measuring currents through tissue thicknesses of up to 25 mm are possible. Preferred tissue thicknesses are 1 mm to 25 mm. More preferred tissue thicknesses are 5 mm to 15 mm. Most preferred tissue thicknesses are 5-10 mm.

OET Bulletin 65 (Edition 97-01), Supplement C (Edition 01-01) (Ref 10) shows the maximum permissible exposure (MPE), which in the case of 900 MHz devices would be 3000 W/sq cm for occupational/controlled exposure and 600 W/sq.cm for general population exposure of the surface of the skin. This translates into 6 W/square millimeter for the devices of the present disclosure. The FCC also determined an individual maximum for radio transmitters of 1 W total for interference reasons. Both of these regulatory limits are based on integrated power, and therefore it is possible to use higher power pulses as long as these integrated power levels are not exceeded.

Figure 7:
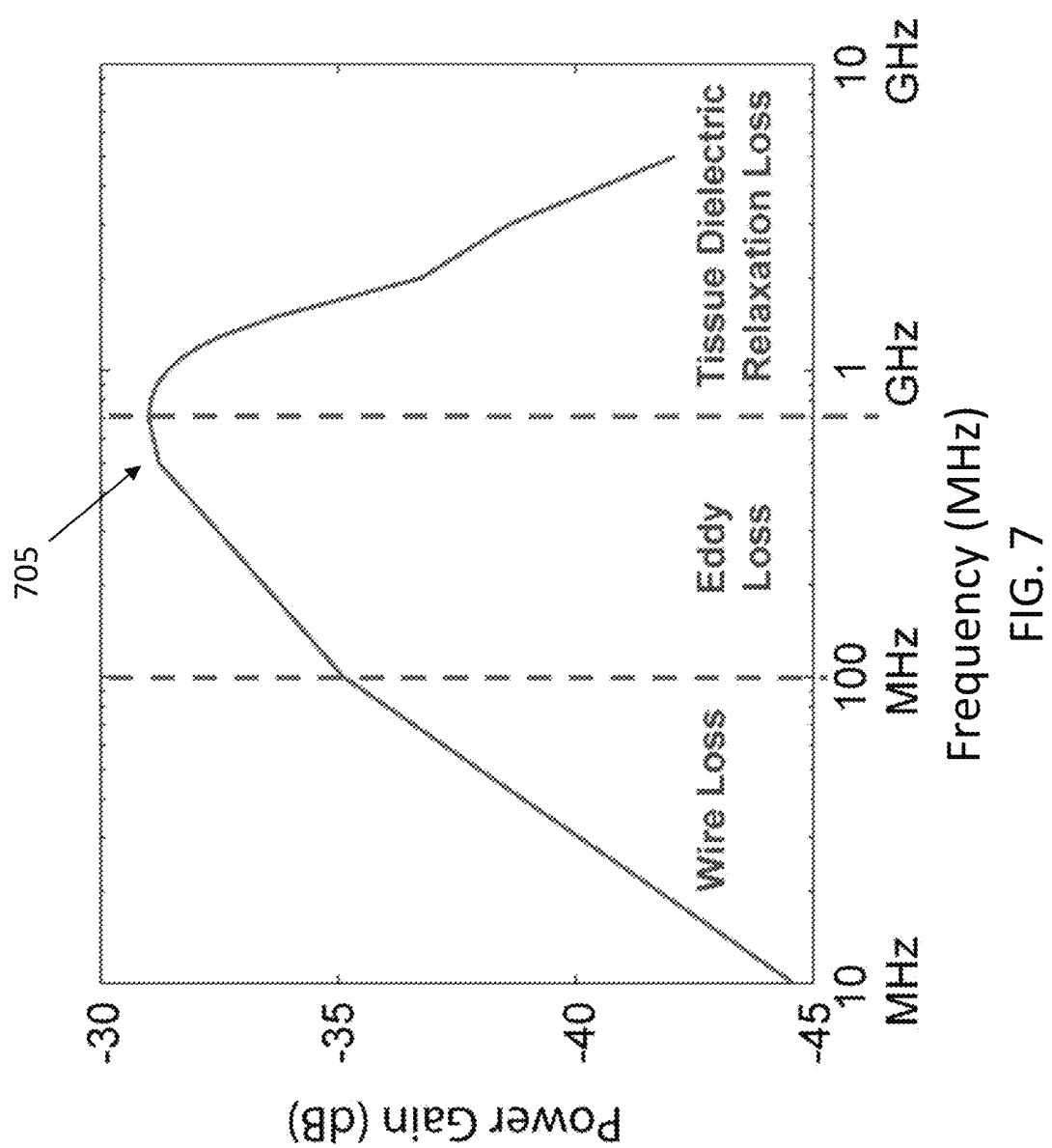
FIG. 7 illustrates a power gain vs frequency plot.

There is a trade-off between frequency, size of the device, and tissue absorption. One skilled in the art would recognize the relationship between wire loss, eddy loss and tissue dielectric relaxation loss. In general, a wire loss refers to the energy lost or dissipated (e.g. a voltage drop) due to resistance in a circuit. Eddy loss refers to the loss of energy due to currents in conductors. Tissue dielectric relaxation loss refers to the changes in dielectric constant and loss index with frequency that are produced by the dielectric polarization within tissue. The two most important are dipole polarization due to polar molecules and interfacial polarization caused by inhomogeneity in the materials. Dielectric constant and loss index vary with frequency. In FIG. 7, the absorption of microwave radiation in tissue is illustrated, as a function of frequency. As can be seen in FIG. 7, the absorption typically increases as the frequency increases, and this would lead to the use of lower frequencies. Indeed, radio transmitter tags typically transmit at low frequencies (100 kHz), as they can be relatively large. However, in some embodiments the sensors of the present disclosure are constrained by the maximum size of an injectable device of approximately 1 mm, and the sizes of the devices and antennas are, in some embodiments, too small for efficient microwave reception. This issue can be important as, in some embodiments, an external power coil is used, which inductively couples to the coil on the sensor chips to power the devices. Therefore, an efficient power transfer mechanism is required. Thus, the trade-off between size and absorption depth has resulted, in some embodiments, in using frequencies around 900 MHz, or the peak (705) of the power gain vs frequency plot.

In some embodiments, wireless power and communications between the sensor and the reader occur by matching, in near-field, a set of two inductive coils. One of the coils is located in the reader and the other in the sensor. Current flow through the reader coil induces a corresponding current in the sensor coil when these are critically coupled, for example at a frequency of 800-900 MHz. Communication can be established when the reader sends a tag signal to the sensor, and the sensor responds with an updated current reading. By monitoring the RF-power transmitted from the reader to the chip, it is possible to establish a two-way communications link, in which reflected power is modulated by the sensor chip. To communicate with the reader, the sensor circuit reflects the input power in short pulses, resulting in digital pulse trains comprising a series of changes in reflective power as measured by the reader. In another embodiment, the entire cage could be composed of coils providing for continuous current flow and continuous interrogation of the sensor chip.

During measurement, the ion current on the working electrode can be read, amplified, and digitized by the CMOS electronic circuit. This measurement can then be transmitted, for example, as an 8-bit binary number to the reader by using a pulse-width modulated format, in which wider pulses encode 1 s, while shorter pulses encode 0 s. As each sensor responds to a separate tag signal, several sensors can be deployed in close proximity on the same animal, yet measured separately. This process also avoids the chemical complexity of Ag/AgCl electrodes by using more durable Pt/PtOx electrodes, therefore extending the lifetime of the sensors. Other possible reference electrodes can include, but are not limited to: gold, copper-copper sulfate, platinum, platinum oxide, and palladium hydrogen.

In typical sensors, the active enzyme is immobilized in a glutaraldehyde/BSA binding layer that is then covered with an outer membrane filter layer to regulate and recycle the oxygen required by the enzyme reaction. In one embodiment, the outer membrane is composed of polyurethane. Outer membrane filter layers also improve selectivity by excluding interferent molecules, such as acetaminophen, urate, cysteine, bilirubin and ascorbic acid.

Figure 2:
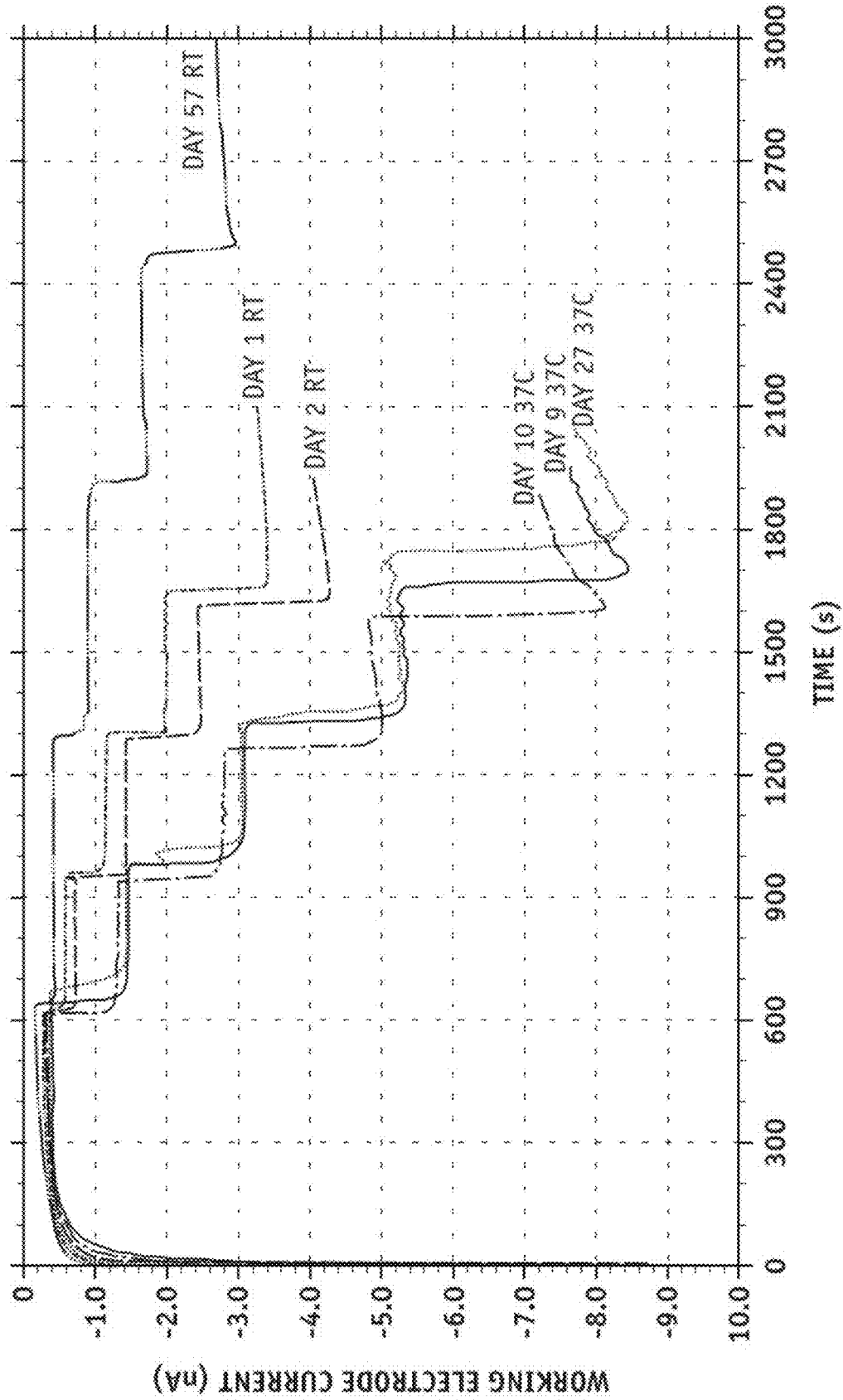
FIG. 2 illustrates typical in vitro glucose monitoring results as a function of time.

FIG. 2 illustrates the response of a typical glucose sensor described above to in vitro glucose monitoring as a function of time. These data show a linear response in the clinically relevant range, for approximately 2 months. It is possible to add enzymes designed to measure other metabolites on the microsensor platform.

One of the main problems resulting from miniaturization of electrochemical sensors is the reduction of the surface area of the working electrode and the corresponding reduction in the signal to noise read by the devices. The approach described in the present disclosure to address this problem is to increase the area of the electro-chemical electrodes geometrically, which can also improve oxygen recycling and increase the number of enzyme molecules accommodated in the layer. The increase in the area of the electrodes can be accomplished in several different ways. In some embodiments, nanostructures are etched into the electrode. For example, nanopillars fabricated into the surface of the electrode can increase its surface area significantly. In some embodiments, the nanopillars may have a diameter of 100 nm, and can increase the surface area by approximately 100 fold. The corresponding electrode response (in this example, from a glucose oxidase reaction) shows a 100 fold increase in signal. This, in turn, enables a reduction in the contact area by the same factor. In other words, the area occupied by the electrode is decreased, and nanopillars are fabricated into its top surface. The nanopillars enhance the electrode response, making up the decrease caused by the reduced area occupied by the electrode.

In some embodiments, the working electrode is coated with a thin ion-selective membrane or ionophore, and can also be used to measure ion concentrations. For example, ionophores can selectively absorb $K^+$, $Na^+$, $H^+$, $OH^-$, and $Cl^-$, and the ion concentration is determined through the corresponding change in voltage on the electrodes. Robust and ion-specific ionophores are commercially available, and make it possible to fabricate an ion microsensor chip with $\mu V$ sensitivity. Possible ionophores used in the sensors of the present disclosure can include, but are not limited to: $Na^+$, $Ca^{2+}$, $K^+$, $Mg^+$, $H^+$, $Zn^+$, $Mn^{2+}$, $Cl^{2+}$, $PO_4^{3-}$, $HPO_4^{2-}$, $H_2PO_4^-$, $CO_3^{2-}$, $HCO_3^-$, and $OH^-$.

Figure 3:
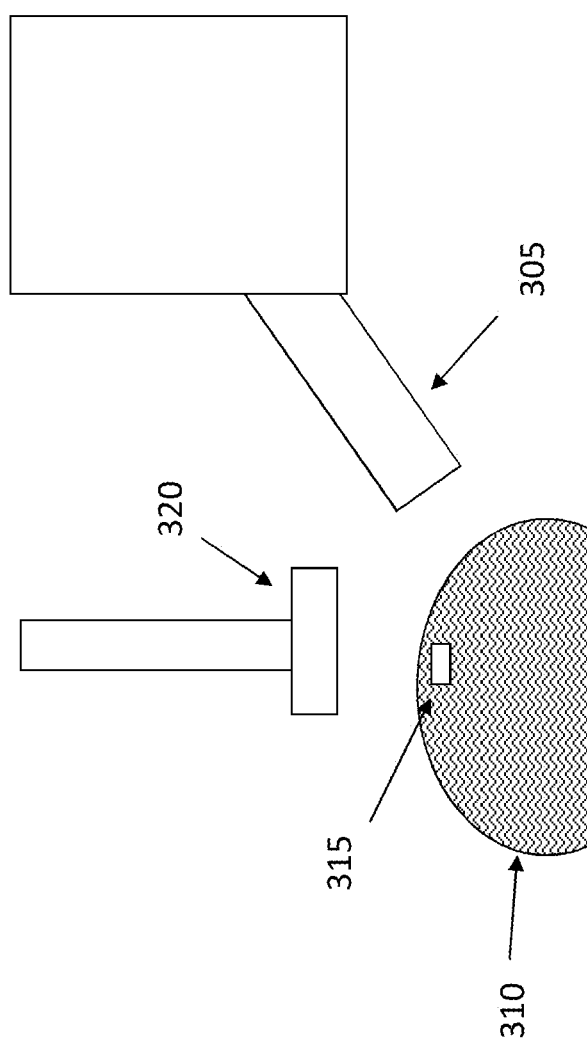
FIG. 3 illustrates location of a feeder in proximity to a drinking tube.

Typical cage designs include feeders and drinking tubes, which the animals use whenever desired. In some embodiments, reader coils can be outfitted in proximity to the feeder or drinking tube, in such a way that the RF tag microsensors embedded in the animal are read when in proximity to the feeder or drinking tube. For example, the data relating to biological parameters in an animal can be acquired when the microsensor embedded in its brain is close to the drinking fountain. An exemplary approach is shown in FIG. 3, where a drinking tube (305) in a smart cage is located in proximity to a reader device (320). When the laboratory animal (310), with an implanted sensor (315), approaches the tube (305), the microsensor can be read by the reader. The reader can be located at a distance from the tube such that the reader is located in proximity to the sensor when the animal is drinking. Therefore, the dimensions of an average laboratory animal can be taken into account when positioning and orienting the reader within the smart cage.

Figure 4:
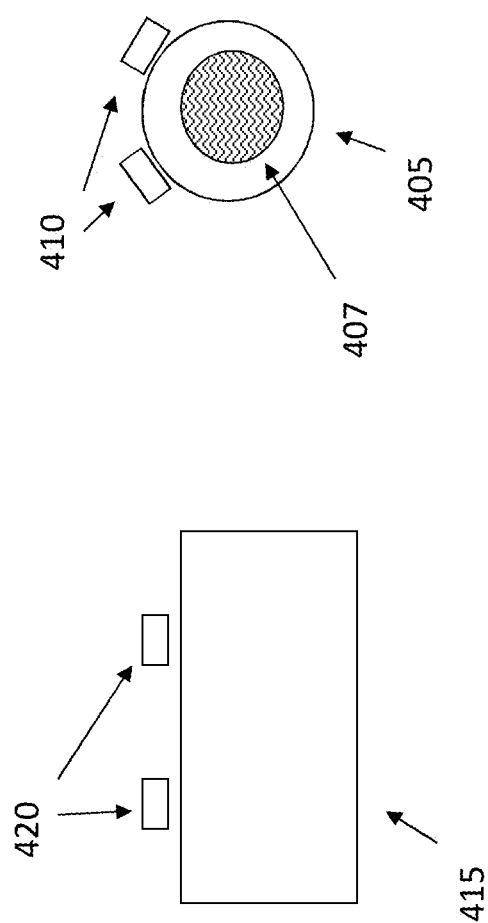
FIG. 4 illustrates a tube with reader devices.

The RF reader coils in (320) can be oriented and mounted in such a way that the animal must push against the coil in order to eat and/or drink. Alternatively, a tube can be included into the cage, and the animal must crawl through the tube before eating or drinking. This tube can contain several RF tag readers to measure implanted tags that interrogate the implanted RF tags. For example, FIG. 4 illustrates a front view of the tube (405) with reader devices on the outer surface (410), and an animal within (407). FIG. 4 also illustrates a side view of the tube (415) with reader devices (420). In this embodiment, the animal is kept in the desired position during the time required for powering and reading the sensors, which can be, in some embodiments, about one second. Judicious placement of the sensors and readers enables the frequent interrogation of sensors and automatic logging of the results. Together with camera feedback on animal position, smart cages can capture much of the valuable activity and chemistry information needed for pharmacovigilance. Therefore, in some embodiments, cameras are included in the smart cage to record the animal's behavior.

The pharmacovigilance capabilities described in the present disclosure are very useful for drug discovery activities, and have the potential of revolutionizing the methods of detection, assessment, monitoring and prevention of adverse drug reactions. Pre-clinical animal trials are one of the important requirements in the regulatory approval process of new medications, and will become even more useful as laboratory animals are bred to genetically match the human immune response.

The smart cages described herein can increase the speed of collection of data, as well as improve the convenience of collection, and significantly increase the quantity of data collected from small laboratory animals.

In-vivo sensor lifetime can be limited due to enzyme degradation: In vitro lifetimes of exemplary sensors have been measured as 2-3 months for glucose and >4 weeks for lactate. In vivo results may suffer from immune system response, in which case it is possible to re-optimize enzyme coatings to improve sensor lifetimes.

Wireless communications link from sensor to reader has to be strong enough to allow transmission of data. In this regard, it is possible to note that manual reading of the sensor is possible even through distances of 1 cm with an exemplary reader power of 3 W, which is limited by OSHA exposure standards for continuous RF powered implants. If this communications link is too weak, it is possible to boost that power or change the implantation site of the microsensors.

Figure 6:
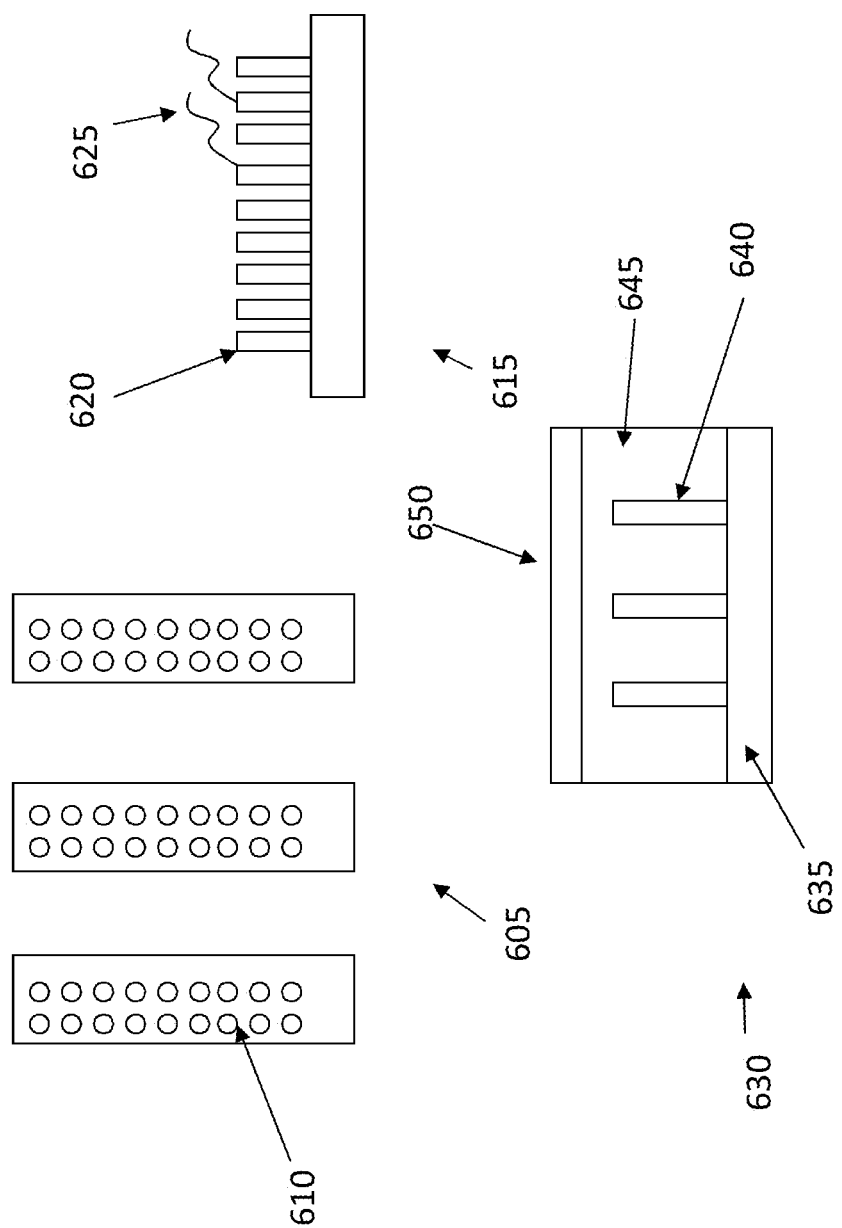
FIG. 6 illustrates an exemplary sensor with nanopillars.

FIG. 6 illustrates an exemplary sensor with nanopillars. In other embodiments, the sensor may be fabricated without nanopillars, using standard electrodes, or a different nanostructure may be used instead of nanopillars. In the exemplary sensor of FIG. 6, a top view (605) illustrates three electrodes comprising nanopillars (610) on their top surface. A side view (615) illustrates exemplary nanopillars (620) on top of the electrode's surface. Enzymes, ion-selective membranes and/or ionophores may be attached to the nanopillars, or to the surface of the electrodes with no nanopillars. For example, the enzymes or ionophores may be attached to the top of the nanopillar, and/or to the sides of the nanopillars. In FIG. 6, exemplary enzymes (625) attached to nanopillars are illustrated. In some embodiments, the ion-selective membrane or other biosensing element may be simply coated on the nanopillar electrode, for example substantially covering the electrodes as illustrated, for example, in (630), illustrating an electrode (635), nanopillars (640) and a membrane (645). In some embodiments, the membrane may comprise an enzyme and a matrix, such as a glutaraldehyde/ bovine serum albumin layer or matrix containing the enzyme. In some embodiments, a filter layer (650) may be coated on the membrane (645), in order to filter interferent molecules that may negatively interfere with the enzyme reactions. In some embodiments, either the receiver or transmitter may be a transceiver.

Possible sensor enzyme systems that may be used in the tags of the present disclosure include, but are not limited to: biorecognition elements specific for glucose, lactate, glutamate, histamine, cortisol, NADH, NAD+, cholesterol, xanthine, sarcosine, spermine, glycolate, choline, urate, GABA, lysine, asparate, nicotine, alcohol, ethanol, D-amino acids, 6-hydroxynicotine, oxalate, putrescine, galactose, pyruvate, poly-amines, acyl coenzyme A, glutathione, glycerolphosphate, gamma-glutamyl-putrescine, nucleosides, adenosine, and glycine.

In some embodiments, the present disclosure describes a system comprising a kit of parts that can be attached to an enclosure or cage, for example to convert a standard enclosure into a smart enclosure as described above in the present disclosure. For example, a kit of parts comprises, in some embodiments, the sensors configured to be implanted or attached to the animals, and at least one reader device which can be attached to some part of an existing enclosure. For example, the reader device may be configured to be attached to a water spout of an existing enclosure, to communicate with the tags attached to the animals within the enclosure.

Figure 8:
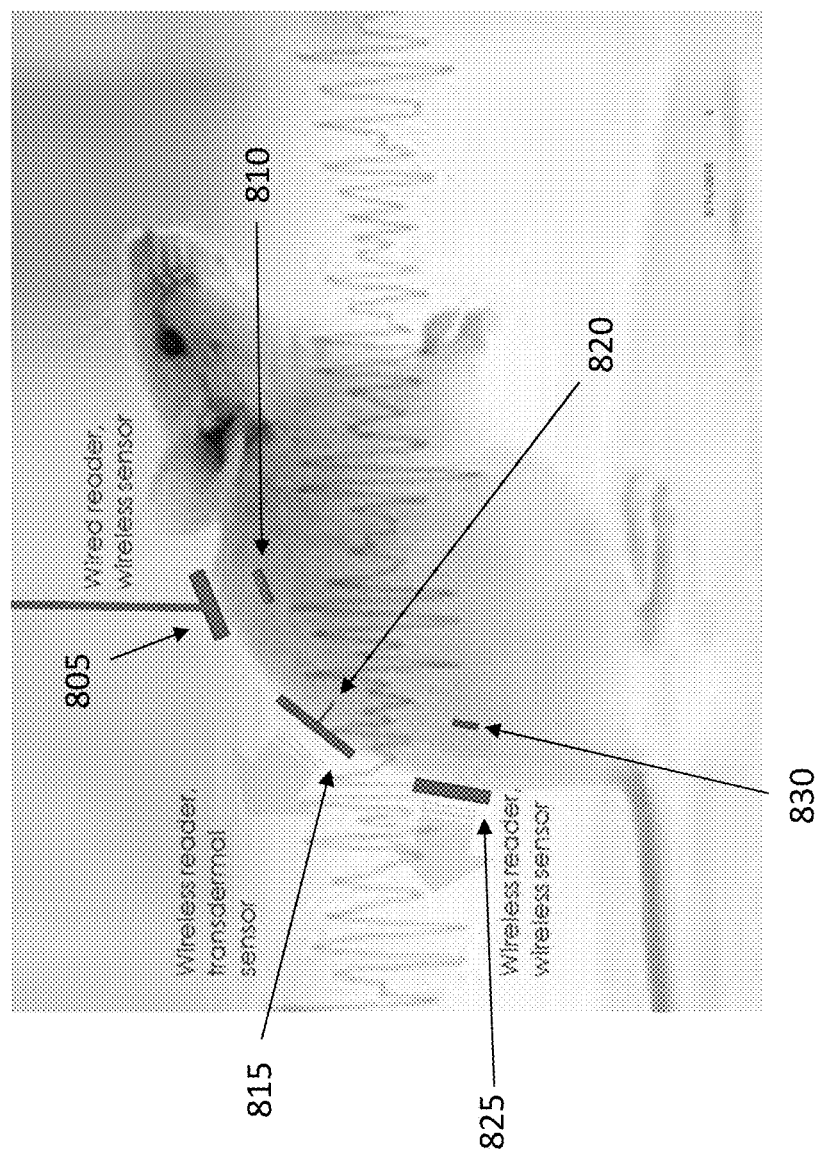
FIG. 8 illustrates different sensor types and locations.

Many different sensor geometries can be integrated into the automated system described as smart cages in the present disclosure. These devices can be broadly divided into transdermal and sub-dermal devices. The simplest wireless devices that can continuously measure metabolic chemistry, that are commercially available today, consist of a wire or needle sensor that is injected through the skin and that is electronically connected to transmitter circuits outside the body. The transmitter is attached to the surface of the skin and obtains its information from the end of the needle inside of the body of the animal. Continuous glucose monitors (CGMs) and brain probes typically operate in this mode. More recently, chemical sensors have emerged that are small enough to be implanted underneath the skin. These subdermal implants enable the measurement of chemistries without the infection risk and with lower scar tissue formation, as the sensors do not move as much relative to the tissue that surrounds them. FIG. 8 shows a schematic of such sensors and how these could be utilized to gather data.

For example, a wired external reader (805) can be located close to a wireless sensor inside the animal (810). For example, the reader (805) may be placed close to a feeding station of the cage. A wireless reader (815) may be integrated with a transdermal sensor (820). A wireless reader (825) may be coupled to a wireless sensor (830).

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

[1] Lubbers, D. W., Oxygen electrodes and optodes and their application in vivo. Advances in experimental medicine and biology 1996, 388, 13-34.
[2] Sakr, Y., Techniques to assess tissue oxygenation in the clinical setting. Transfusion and Apheresis Science 2010, 43 (1), 79-94.
[3] Bickler, P.; Feiner, J.; Rollins, M.; Meng, L., Tissue Oximetry and Clinical Outcomes. Anesthesia and Analgesia 2017, 124 (1), 72-82.
[4] Environmental enrichment in mice decreases anxiety, attenuates stress responses and enhances natural killer cell activity. 2004. Benaroya-Milshtein N, Hollander N, Apter A, Kukulansky T, Raz N, Wilf A, Yaniv I, Pick CG. Eur J Neurosci 20:1341-1347.
[5] Environmental enrichment lowers stress-responsive hormones in singly housed male and female rats. Belz E E, Kennell J S, Czambel R K, Rubin R T, Rhodes M E. Pharmacol 2003. Belz E E, Kennell J S, Czambel R K, Rubin R T, Rhodes M E. Pharmacol Pharmacol Biochem Behav 76:481-486.
[6] National Research Council. 2011. *Guide for the Care and Use of Laboratory Animals: Eighth Edition*. Washington, D.C.: The National Academies Press. https://doi.org/10.17226/12910.
[7] Bayne K A. 2005. Potential for unintended consequences of environmental enrichment for laboratory animals and research results. ILAR J 46:129-139
[8] Novak M A, Meyer J S, Lutz C, Tiefenbacher S. 2006. Deprived environments: Developmental insights from primatology. In: Mason G, Rushen J, eds. Stereotypic Animal Behaviour: Fundamentals and Applications to Welfare. Wallingford, UK: CABI. p 153-189.
[9] Kalliokoski O, Jacobsen K R, Darusman H S, et al. Mice Do Not Habituate to Metabolism Cage Housing—A Three Week Study of Male BALB/c Mice. Reddy H, ed. PLoS ONE. 2013; 8(3):e58460. doi:10.1371/journal.pone.0058460.
[10] "DIRECTIVE 2010/84/EU, Article 101" Ec.Europa.Eu., 2015-10-26

What is claimed is:

1. A system comprising:
   a container configured to contain at least one laboratory animal, the container containing at least one radiofrequency transceiver, the at least one radiofrequency transceiver being a wireless radiofrequency transceiver; and
   at least one sensor configured to read at least one monitorable condition of the at least one laboratory animal, the at least one sensor configured to be attached to the at least one laboratory animal, the at least one sensor comprising at least one radiofrequency transmitter,
   wherein the at least one radiofrequency transmitter comprises at least one coil, the at least one radiofrequency transceiver comprises at least one coil, and the at least one radiofrequency transmitter and the at least one radiofrequency transceiver are configured to communicate and transfer energy through near-field inductive coupling between 800 and 900 MHz;
   wherein the at least one coil is oriented and mounted in the container such that the at least one laboratory animal has to push against the at least one coil in order to reach food and/or drink.

2. The system of claim 1, wherein the at least one sensor is configured to:
   i) be attached to the at least one laboratory animal by an adhesive, or
   ii) be implanted under skin of the at least one laboratory animal.

3. The system of claim 1, wherein the at least one monitorable condition is selected from the group consisting of: position, gait, posture, temperature, oxygenation, local pH, and the concentration of glucose, lactate, glutamate, histamine, cortisol, NADH, NAD+, cholesterol, xanthine, sarcosine, spermine, glycolate, choline, urate, GABA, lysine, asparate, nicotine, alcohol, ethanol, D-amino acids, 6-hydroxynicotine, oxalate, putrescine, galactose, pyruvate, poly-amines, acyl coenzyme A, glutathione, glycerolphosphate, gamma-glutamyl-putrescine, nucleosides, adenosine, sodium, potassium, and glycine.

4. The system of claim 1, wherein the at least one sensor comprises: a potentiostat, a working electrode, a reference electrode, and a counter electrode.

5. The system of claim 4, wherein at least one electrochemically active enzyme or ionophore is coated onto at least one of: a top surface of the working electrode, a top surface of the reference electrode, and a top surface of the counter electrode, the at least one electrochemically active enzyme or ionophore selected to detect an ion or biological molecule in the at least one laboratory animal.

6. The system of claim 5, wherein the working electrode, the reference electrode, and the counter electrode comprise a material selected from the group consisting of: platinum, platinum oxide, gold, copper-copper sulfate, and palladium hydrogen.

7. The system of claim 1, wherein the container comprises a food or water source, and the at least one radiofrequency transceiver is located close to the food or water source and is configured to communicate to the at least one radiofrequency transmitter each time the at least one laboratory animal interacts with the food or water source.

8. The system of claim 5, wherein the at least one electrochemically active enzyme or ionophore comprises glucose oxidase or lactate oxidase, in a glutaraldehyde/bovine serum albumin layer.

9. The system of claim 8, wherein the glutaraldehyde/bovine serum albumin layer is covered with a filter layer configured to regulate and recycle oxygen required by an enzyme reaction involving the electrochemically active enzyme.

10. The system of claim 9, wherein the filter layer comprises polyurethane and is configured to improve selectivity of the at least one sensor, by excluding interferent molecules.

11. The system of claim 10, wherein the interferent molecules are selected from the group consisting of: acetaminophen, urate, cysteine, bilirubin and ascorbic acid.

12. The system of claim 1, wherein the at least one radiofrequency transmitter comprises a plurality of radiofrequency transmitters, each transmitter of the plurality of radiofrequency transmitters being individually identifiable by a code transmitted to the at least one radiofrequency transceiver.

13. The system of claim 5, wherein at least one of: the top surface of the working electrode, the top surface of the reference electrode, and the top surface of the counter electrode comprises nanopillars, and the at least one electrochemically active enzyme or ionophore is coated onto the nanopillars.

14. The system of claim 5, wherein the at least one electrochemically active enzyme or ionophore is an ionophore selected from the group consisting of Na$^+$, Ca$^{2+}$, K$^+$, Mg$^+$, H$^+$, Zn$^+$, Mn$^{2+}$, Cu$^{2+}$, Cl$^-$, PO$_4^{3-}$, HPO$_4^{2-}$, H$_2$PO$_4^-$, CO$_3^{2-}$, HCO$_3^-$, and OH$^-$.

15. The system of claim 5, wherein the at least one electrochemically active enzyme or ionophore is configured to selectively absorb at least one ion selected from the group consisted of K$^+$, Na$^+$, H$^+$, OH$^-$, and Cl$^-$.

16. The system of claim 5, wherein the at least one electrochemically active enzyme or ionophore is a biorecognition element specific for an organic molecule selected from the group consisting of glucose, lactate, glutamate, histamine, cortisol, NADH, NAD+, cholesterol, xanthine, sarcosine, spermine, glycolate, choline, urate, GABA, lysine, asparate, nicotine, alcohol, ethanol, D-amino acids, 6-hydroxynicotine, oxalate, putrescine, galactose, pyruvate, poly-amines, acyl coenzyme A, glutathione, glycerolphosphate, gamma-glutamyl-putrescine, nucleosides, adenosine, and glycine.

17. A method comprising:
providing a container configured to contain at least one laboratory animal, the container further containing at least one radiofrequency transceiver, the at least one radiofrequency transceiver being a wireless radiofrequency transceiver;
providing at least one sensor configured to read at least one monitorable condition of the at least one laboratory animal, the at least one sensor configured to be attached to the at least one laboratory animal, the at least one sensor comprising at least one radiofrequency transmitter;
attaching or implanting the at least one sensor to the at least one laboratory animal; and
detecting at least one monitorable condition in the at least one laboratory animal by the at least one radiofrequency transceiver communicating with the at least one radiofrequency transmitter,
wherein the at least one radiofrequency transmitter comprises at least one coil, the at least one radiofrequency transceiver comprises at least one coil, and the at least one radiofrequency transmitter and the at least one radiofrequency transceiver are configured to communicate and transfer energy through near-field inductive coupling between 800 and 900 MHz; wherein the at least one coil is oriented and mounted in the container such that the at least one laboratory animal has to push against the at least one coil in order to reach food and/or drink.

18. The method of claim 17, wherein:
the at least one sensor comprises: a potentiostat, a working electrode, a reference electrode, and a counter electrode, and
the at least one monitorable condition is selected from the group consisting of: position, gait, posture, temperature, oxygenation, local pH, and the concentration of glucose, lactate, glutamate, histamine, cortisol, NADH, NAD+, cholesterol, xanthine, sarcosine, spermine, glycolate, choline, urate, GABA, lysine, asparate, nicotine, alcohol, ethanol, D-amino acids, 6-hydroxynicotine, oxalate, putrescine, galactose, pyruvate, poly-amines, acyl coenzyme A, glutathione, glycerolphosphate, gamma-glutamyl-putrescine, nucleosides, adenosine, sodium, potassium, and glycine.

19. The method of claim 18, further comprising:
coating at least one of: a top surface of the working electrode, a top surface of the reference electrode, and a top surface of the counter electrode with at least one electrochemically active enzyme or ionophore, the at least one electrochemically active enzyme or ionophore selected to detect an ion or biological molecule in the at least one laboratory animal.

20. The method of claim 19, wherein the at least one electrochemically active enzyme or ionophore is:
an ionophore selected from the group consisting of: Na$^+$, Ca$^{2+}$, K$^+$, Mg$^+$, H$^+$, Zn$^+$, Mn$^{2+}$, Cu$^{2+}$, Cl$^-$, PO$_4^{3-}$, HPO$_4^{2-}$, H$_2$PO$_4^-$, CO$_3^{2-}$, HCO$_3^-$, and OH$^-$, or
a biorecognition element specific for an organic molecule selected from the group consisting of: glucose, lactate, glutamate, histamine, cortisol, NADH, NAD+, cholesterol, xanthine, sarcosine, spermine, glycolate, choline, urate, GABA, lysine, asparate, nicotine, alcohol, ethanol, D-amino acids, 6-hydroxynicotine, oxalate, putrescine, galactose, pyruvate, poly-amines, acyl coenzyme A, glutathione, glycerolphosphate, gamma-glutamyl-putrescine, nucleosides, adenosine, and glycine.

21. The method of claim 19, further comprising fabricating nanopillars on at least one of: the top surface of the working electrode, the top surface of the reference electrode, and the top surface of the counter electrode, wherein coating with the at least one electrochemically active enzyme or ionophore is onto the nanopillars.

22. A system comprising:
at least one wireless radiofrequency transceiver configured to be attached inside of a container, the container configured to contain at least one laboratory animal; and
at least one sensor configured to read at least one monitorable condition of the at least one laboratory animal, the at least one sensor configured to be attached to the at least one laboratory animal, the at least one sensor comprising at least one radiofrequency transmitter,
wherein the at least one radiofrequency transmitter comprises at least one coil, the at least one radiofrequency transceiver comprises at least one coil, and the at least one radiofrequency transmitter and the at least one radiofrequency transceiver are configured to communicate and transfer energy through near-field inductive coupling between 800 and 900 MHz; wherein the at least one coil is oriented and mounted in the container such that the at least one laboratory animal has to push against the at least one coil in order to reach food and/or drink.

\* \* \* \* \*